(12) United States Patent
Woelfert et al.

(10) Patent No.: US 7,915,444 B2
(45) Date of Patent: Mar. 29, 2011

(54) METHOD FOR PRODUCING DIISOCYANATES

(75) Inventors: Andreas Woelfert, Bad Rappenau (DE);
Carsten Knoesche, Niederkirchen (DE);
Manfred Heilig, Speyer (DE); Eckhard Stroefer, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/997,412

(22) PCT Filed: Jul. 31, 2006

(86) PCT No.: PCT/EP2006/064850
§ 371 (c)(1),
(2), (4) Date: Jan. 31, 2008

(87) PCT Pub. No.: WO2007/014936
PCT Pub. Date: Feb. 8, 2007

(65) Prior Publication Data
US 2008/0200722 A1    Aug. 21, 2008

(30) Foreign Application Priority Data

Aug. 4, 2005   (DE) .................... 10 2005 037 328

(51) Int. Cl.
*C07C 263/10*   (2006.01)

(52) U.S. Cl. .................................... 560/347
(58) Field of Classification Search ................ 560/347
See application file for complete search history.

(56) References Cited

U.S. PATENT DOCUMENTS

| | | | | |
|---|---|---|---|---|
| 4,581,174 A | * | 4/1986 | Ohlinger et al. | 560/347 |
| 5,391,683 A | * | 2/1995 | Joulak et al. | 528/67 |
| 5,679,839 A | * | 10/1997 | Armand et al. | 560/347 |

FOREIGN PATENT DOCUMENTS

| | | |
|---|---|---|
| DE | 102 61 191 | 7/2004 |
| EP | 0 150 435 | 8/1985 |
| EP | 0 570 799 | 11/1993 |
| EP | 0 593 334 | 4/1994 |
| EP | 0 699 657 | 3/1996 |
| EP | 0 749 958 | 12/1996 |
| EP | 1 078 918 | 2/2001 |
| GB | 737 442 | 9/1955 |
| WO | 2004 058689 | 7/2004 |
| WO | 2005 115974 | 12/2005 |
| WO | 2005 123665 | 12/2005 |

OTHER PUBLICATIONS

U.S. Appl. No. 12/446,460, filed Apr. 21, 2009, Boehling, et al.

* cited by examiner

*Primary Examiner* — Sikarl A Witherspoon
(74) *Attorney, Agent, or Firm* — Oblon, Spivak, McClelland, Maier & Neustadt, L.L.P.

(57) ABSTRACT

The present invention relates to a process for preparing diisocyanates from diamines and phosgene in the gas phase.

21 Claims, 1 Drawing Sheet

METHOD FOR PRODUCING DIISOCYANATES

Figure 1:
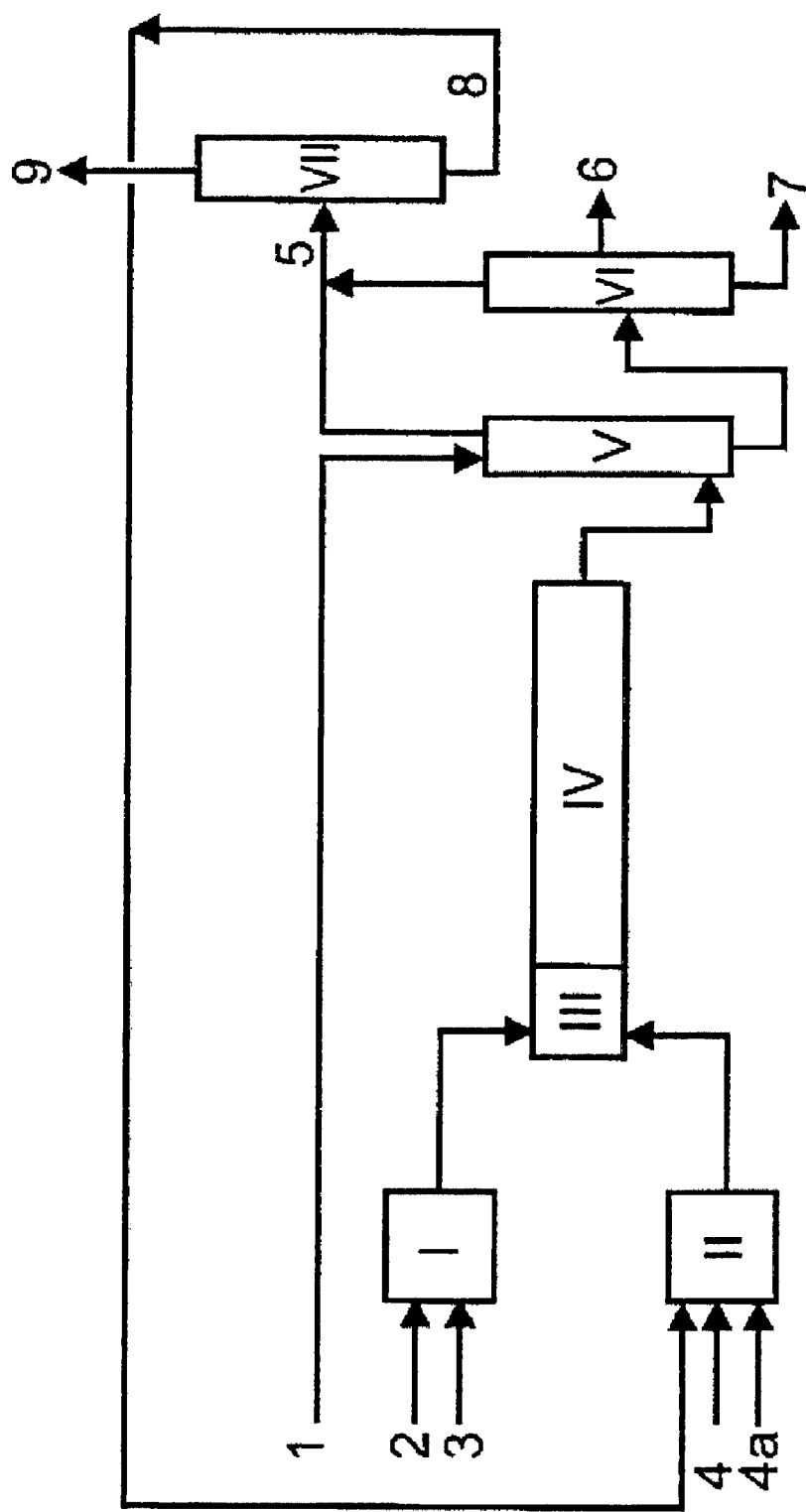

The present invention relates to a process for preparing diisocyanates from diamines and phosgene in the gas phase.

EP 570799, Example 1, describes the work-up of a reaction mixture obtained by gas-phase phosgenation by means of a scrubbing tower through which water is trickled for removal of phosgene and hydrogen chloride.

Excess phosgene and hydrogen chloride are destroyed by such a work-up and can no longer be used beneficially in the reaction.

EP 593334 B1 and EP 699657 B1 disclose the possibility of utilizing or destroying phosgene or hydrogen chloride gas, but without going into the specific problems associated with recirculated phosgene.

EP 749 958 B1 [0018] and EP 1078918 B1 [0018] mention the possibility of recovering excess phosgene after completion of a gas-phase phosgenation of triamines and reusing recovered hydrogen chloride gas in the phosgene synthesis.

Here too, no detailed information about the recovered phosgene is given.

U.S. Pat. No. 4,581,174 describes the continuous preparation of organic monoisocyanates and/or polyisocyanates by phosgenation of a primary amine in a mixing circuit with partial recirculation of the isocyanate-comprising reaction mixture, with the proportion of HC, in the recirculated mixture being less than 0.5%. Here too, the continuous recirculation of the isocyanate to the reaction zone comprising free amine promotes urea formation. The urea which precipitates endangers stable operation of the process.

GB 737 442 describes the recovery of phosgene from the isocyanate synthesis. The recovered phosgene has an HCl content of from 0.5 to 0.7%.

DE 10261191 A1 and WO 2004/58689 describe phosgenations in which the HCl content of the phosgene-comprising feed stream is less than 0.4 or more than 0.8% by weight.

These documents do not differentiate between the problems of gas-phase phosgenation and liquid-phase phosgenation and are preferentially directed only at liquid-phase phosgenation.

Since recirculated phosgene always comprises a certain proportion of hydrogen chloride, the recirculation of such phosgene to the phosgenation of amines results in formation of the corresponding amine hydrochlorides from amine and hydrogen chloride. These amine hydrochlorides are often sparingly soluble in the reaction mixture of a phosgenation carried out in the liquid phase, but this generally does not bring serious disadvantages, for example as a result of deposit formation, with it since any deposits are quickly removed again by the motion of the liquid phase. On the contrary, it is even a widespread practice to reduce the reactivity of the amine used toward phosgene by using the amine as hydrochloride in the phosgenation.

However, the problem in a phosgenation in the gas phase is a completely different one: since the gaseous reaction mixture does not have a sufficient abrasive action, deposits which have precipitated, for example of amine hydrochlorides, cannot readily be removed again, so that deposits alter heat transfer or the flow through the components concerned in an undesirable way.

It was an object of the invention to provide a process which permits a mode of operation in the reaction of diamines with phosgene to form the corresponding diisocyanates and hydrogen chloride (HCl) in the gas phase, in which solids depositing during the reaction can be avoided so that a high space-time yield can be obtained.

This object has been achieved by a process for preparing diisocyanates by reacting the corresponding diamines with phosgene in a stoichiometric excess of phosgene in at least one reaction zone, wherein the reaction conditions are selected so that at least the reaction components diamine, diisocyanate and phosgene are gaseous under these conditions and at least one diamine-comprising gas stream and at least one phosgene-comprising gas stream are fed into the reaction zone, excess phosgene and hydrogen chloride gas (HCl) formed are separated off from the essentially gaseous reaction mixture obtained, the excess phosgene which has been separated off is at least partly recirculated to the reaction, and hydrogen chloride is separated off from the recirculated phosgene stream so that the mass fraction of hydrogen chloride in the phosgene-comprising stream prior to mixing with the amine-comprising stream is less than 15% by weight.

In the gas-phase phosgenation, the invention seeks to ensure that the compounds occurring during the course of the reaction, i.e. starting materials (diamine and phosgene), intermediates (in particular the monocarbamoyl and dicarbamoyl chlorides from those intermediates), end products (diisocyanate) and also possibly inert compounds which have been introduced, remain in the gas phase under the reaction conditions. Should these or other components precipitate from the gas phase, e.g. on the reactor wall or other components of the apparatus, these deposits can alter heat transfer or the flow of the components concerned in an undesirable way. This is particularly true of amine hydrochlorides which can be formed by reaction of free amino groups with hydrogen chloride (HCl), since the resulting amine hydrochlorides precipitate easily and are difficult to evaporate again.

The process of the invention enables the formation of amine hydrochlorides to be reduced significantly, so that the risk of deposit formation in the reactor is reduced.

In the process of the invention, the reaction of phosgene with diamine occurs in the gas phase. For the purposes of the present invention, a reaction in the gas phase means that the feed streams react with one another in the gaseous state.

Diisocyanates which can be prepared by the process of the invention can be aromatic, cycloaliphatic or aliphatic diisocyanates.

Cycloaliphatic isocyanates are ones which comprise at least one cycloaliphatic ring system.

Aliphatic isocyanates are ones which have exclusively isocyanate groups which are bound to straight or branched chains.

Aromatic isocyanates are ones which have at least one isocyanate group bound to at least one aromatic ring system.

For the purposes of the present patent application, the term (cyclo)aliphatic isocyanates is used as an abbreviation for cycloaliphatic and/or aliphatic isocyanates.

Examples of aromatic diisocyanates are preferably ones having 6-20 carbon atoms, for example monomeric methylenedi(phenyl isocyanate) (MDI), tolylene 2,4- and/or 2,6-diisocyanate (TDI) and naphthylene diisocyanate (NDI).

Diisocyanates are preferably (cyclo)aliphatic diisocyanates, particularly preferably (cyclo)aliphatic diisocyanates having from 4 to 20 carbon atoms.

Examples of customary diisocyanates are aliphatic diisocyanates such as tetramethylene diisocyanate, hexamethylene diisocyanate (1,6-diisocyanatohexane), octamethylene 1,8-diisocyanate, decamethylene 1,10-diisocyanate, dodecamethylene 1,12-diisocyanate, tetradecamethylene 1,14-diisocyanate, derivatives of lysine diisocyanate, tetramethylxylylene diisocyanate (TMXDI), trimethylhexane diisocyanate or tetramethylhexane diisocyanate, and also 3 (or 4), 8 (or 9)-bis(isocyanatomethyl)-tricyclo[5.2.1.0$^{2.6}$]decane isomer mixtures, and also cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5- trimethyl-5-(isocyanatomethyl)cyclohexane(isophorone diisocyanate), 1,3- or 1,4-bis(iso-cyanatomethyl) cyclohexane, 2,4- or 2,6-diisocyanato-1-methylcyclohexane.

Preference is given to 1,6-diisocyanatohexane, 1-isocyanato-3,3,5-trimethyl-5-(isocyanatomethyl)cyclohexane, 4,4'-di(isocyanatocyclohexyl)methane and tolylene diisocyanate isomer mixtures. Particular preference is given to 1,6-diisocyanatohexane, 1-isocyanato-3,3,5-trimethyl-5-(isocyanatomethyl)cyclohexane and 4,4'-di(isocyanatocyclohexyl) methane.

In the process of the invention, it is possible to use amines which can preferably be brought into the gas phase without decomposition for the reaction to form the corresponding diisocyanates. Here, amines, in particular diamines, based on aliphatic or cycloaliphatic hydrocarbons having from 2 to 18 carbon atoms are particularly useful. Examples are 1,6-diaminohexane, 1-amino-3,3,5-trimethyl-5-aminomethylcyclohexane (IPDA) and 4,4'-diaminodicyclohexylmethane. Preference is given to using 1,6-diaminohexane (HDA).

It is likewise possible to use aromatic amines which can preferably be brought into the gas phase without decomposition for the process of the invention. Examples of preferred aromatic amines are toluenediamine (TDA), as 2,4 or 2,6 isomers or a mixture thereof, diaminobenzene, R,S-1-phenylethylamine, 1-methyl-3-phenylpropylamine, 2,6-xylidine, bis(3-aminophenyl) sulfone, napthylenediamine (NDA) and 2,4'- or 4,4'-methylene(diphenylamine) (MDA) or isomer mixtures thereof. Among these, preference is given to the diamines, particularly preferably 2,4- and/or 2,6-TDA.

The starting materials or only one of them can be introduced together with an inert medium into the reaction space.

An additional inert medium can be concomitantly used in the process of the invention. The inert medium is a medium which is in gaseous form in the reaction space at the reaction temperature and does not react with the compounds occurring during the course of the reaction. The inert medium is generally mixed with amine and/or phosgene prior to the reaction, but can also be introduced separately from the feed streams. For example, nitrogen, noble gases such as helium or argon or aromatics such as chlorobenzene, dichlorobenzene, xylene, carbon dioxide or carbon monoxide can be used. Preference is given to using nitrogen and/or chlorobenzene as inert medium.

In general, the inert medium is used in such an amount that the ratio of the gas volumes of inert medium to amine and/or to phosgene is greater than 0.0001 and up to 30, particularly preferably greater than 0.01 and up to 15, particularly preferably greater than 0.1 and up to 5.

The inert medium is preferably introduced together with the diamine into the reaction space.

The introduction of phosgene via the phosgene-comprising stream into the reaction space can also be carried out by feeding in a plurality of phosgene-comprising substreams instead of a single phosgene-comprising stream. In such a case, the phosgene-comprising substreams are added together to give a total phosgene-comprising total stream and the mass fraction of hydrogen chloride in the phosgene-comprising total stream is derived from the mass fractions of hydrogen chloride in the individual phosgene-comprising substreams under the assumption of maintenance of the molecule without reaction. In this case, the value of the hydrogen chloride mass fraction calculated in this way is used in the conceptual total phosgene stream.

Such substreams can be introduced in the following way:
  Various phosgene-comprising substreams, for example recirculated phosgene and fresh phosgene, can be combined to form a phosgene-comprising total stream before the introduction and then be fed into the reaction space.
  A plurality of substreams, which can in each case be recirculated phosgene, fresh phosgene or a mixture thereof, can be fed into the reaction space at the same point, for example via a plurality of nozzles which are arranged in parallel around a central nozzle, as described, for example, in EP 1449826 A1, or by multiple injection into an annular space for mixing before this stream is with an amine-comprising stream metered in via a central nozzle.
  A plurality of substreams, which can in each case be recirculated phosgene, fresh phosgene or a mixture thereof, can be introduced into the reaction space at various points, so that further phosgene is introduced during the course of the reaction.

For the present purposes, the term "fresh phosgene" refers to a phosgene-comprising stream which has not been recirculated from a phosgenation process but has after the synthesis of the phosgene, usually from chlorine and carbon monoxide, not gone through any reaction stage involving a phosgene reaction in which the phosgene prepared in the phosgene synthesis is reacted to an extent of greater than 5%.

If one or more additional, gaseous phosgene-free or amine-free inert streams are fed into the reaction space, then these are, in carrying out the process of the invention, included as a substream of the phosgene-comprising total stream in the calculation of the phosgene-comprising total stream.

To carry out the process of the invention, it can be advantageous to preheat the streams of the reactants prior to mixing, usually to temperatures of at least 200° C., preferably at least 260° C. and particularly preferably at least 300° C.

In the amine reservoir, the amine is brought into the gas phase, preferably together with an inert medium such as nitrogen as carrier gas, and fed into the mixing unit. However, the amine can also be vaporized directly without use of an inert medium. Phosgene from the phosgene reservoir is likewise brought into the gas phase, if appropriate together with an inert medium, and introduced into the mixing unit.

In the process of the invention, mixing of the reactants occurs in a mixing device in which the reaction stream passed through the mixing device is subjected to high shear. As mixing device, preference is given to using a static mixing device or a mixing nozzle which is installed upstream of the reactor. Particular preference is given to using a mixing nozzle.

The type of mixing plays no role for the purposes of the invention and can be carried out in any way, for example as described in EP-BL 699657, EP-A2 1319655, column 1, line 54 to column 2, line 24 and column 4, lines 16-40, EP-A1 1275640, column 3, line 27—column 4, line 5, EP-A2 1362847, column 2, line 19—column 3, line 51 and column 4, line 40—column 5, line 12, which are each hereby expressly incorporated by reference into the present disclosure.

According to the invention, phosgene is used in an excess over amino groups. The molar ratio of phosgene to amino groups is usually from 1.1:1 to 20:1, preferably from 1.2:1 to 5:1.

After mixing in the mixing unit, the gaseous mixture of phosgene, amine and, if appropriate, inert medium is introduced into the reactor comprising the reaction space.

The reaction of phosgene with amine occurs in a reaction space which is generally located in a reactor, i.e. the reaction space is, for the purposes of the present invention, the region in which a part of the reaction of the starting materials and intermediates and/or the products which is relevant to the yield of the process occurs and in which, for example, at least 0.5 mol % of the amine used is consumed and/or the corresponding isocyanate is formed, preferably at least 1 mol %, particularly preferably at least 3 mol %, very particularly preferably at least 5 mol %, in particular at least 7 mol % and especially at least 10 mol %, of the amine used is consumed and/or the corresponding isocyanate is formed.

For the purposes of the present invention, the reactor is the technical apparatus which comprises the reaction space. The reaction space can be any customary reaction space which is known from the prior art and is suitable for a noncatalytic, single-phase gas reaction, preferably for a continuous noncatalytic, single-phase gas reaction, and will withstand the moderate pressures required. Suitable materials for contact with the reaction mixture are, for example, metals such as steel, tantalum, silver or copper, glass, ceramic, enamel or homogeneous or heterogeneous mixtures thereof. Preference is given to using steel reactors. The walls of the reactor can be smooth or profiled. Suitable profiles are, for example, grooves or corrugations.

The reaction zone is the sum of all reaction spaces in which the diamine is converted essentially completely into the diisocyanate, i.e. preferably to at least 95 mol % of the amino groups used, particularly preferably at least 97 mol %, very particularly preferably at least 98 mol %, in particular at least 99 mol %, especially at least 99.5 mol % and even at least 99.8 mol %. The reaction can be carried out in one or more reaction zones of which each individual reaction zone is supplied with at least one diamine-comprising gas stream and at least one phosgene-comprising gas stream.

It is generally possible to use the reactor construction types known from the prior art. Examples of reactors are known from EP-B1 289840, column 3, line 49—column 4, line 25, EP-B1 593334, WO 2004/026813, page 3, line 24—page 6, line 10, WO 03/045900, page 3, line 34—page 6, line 15, EP-A1 1275639, column 4, line 17-column 5, line 17 and EP-B1 570799, column 2, line 1—column 3, line 42, which are hereby expressly incorporated by reference into the present disclosure.

Preference is given to using tube reactors.

It is likewise possible to use essentially cuboidal reaction spaces, for example plate reactors or plate reaction spaces. A particularly preferred plate reactor has a ratio of width to height of at least 2:1, preferably at least 3:1, particularly preferably at least 5:1 and in particular at least 10:1. The upper limit of the ratio of width to height depends on the desired capacity of the reaction space and is in principle not subject to any restrictions. Reaction spaces having a ratio of width to height up to a maximum of 5000:1, preferably 1000:1 have been found to be technically sensible.

The reaction of phosgene with amine in the reaction space occurs at absolute pressures of from >0.1 bar to <20 bar, preferably from 0.5 bar to 10 bar, particularly preferably from 0.7 bar to 5 bar, in particular from 0.8 to 3 bar.

In general, the pressure in the feed lines to the mixing device is higher than the abovementioned pressure in the reactor. Depending on the choice of mixing device, the pressure decreases in the mixing device. The pressure in the feed lines is preferably from 20 to 2000 mbar, particularly preferably from 30 to 1000 mbar, higher than in the reaction space.

In a preferred embodiment, the reactor comprises a bundle of reactors. In one possible embodiment, the mixing unit does not have to be an independent device, but instead it can be advantageous to integrate the mixing unit into the reactor. An example of an integrated unit of mixing unit and reactor is a tube reactor with flanged-on nozzles.

In general, the pressure in the work-up apparatus is lower than in the reaction space. The pressure is preferably from 50 to 500 mbar, particularly preferably from 80 to 150 mbar, lower than in the reaction space.

In the process of the invention, the reaction of phosgene with amine occurs in the gas phase. For the purposes of the present invention, a reaction in the gas phase means that the feed streams and intermediates react with one another in the gaseous state to form the products and remain in the gas phase during the course of the reaction while passing through the reaction space to an extent of at least 95%, preferably at least 98%, particularly preferably at least 99%, very particularly preferably at least 99.5%, in particular at least 99.8% and especially at least 99.9%.

Intermediates are, for example, the monoaminomonocarbamoyl chlorides, dicarbamoyl chlorides, monoamino monoisocyanates and monoisocyanatomonocarbamoyl chlorides formed from the diamines and also the hydrochlorides of the amino compounds.

In the process of the invention, the temperature in the reaction space is selected so that it is above the boiling point of the diamine used, based on the pressures prevailing in the reaction space. Depending on the amine used and the pressure set, an advantageous temperature in the reaction space is usually more than 200° C., preferably more than 260° C. and particularly preferably more than 300° C. The temperature is generally up to 600° C., preferably up to 570° C.

The mean contact time of the reaction mixture in the process of the invention is generally from 0.001 second to <5 seconds, preferably from >0.01 second to <3 seconds, particularly preferably from >0.02 second to <1.5 seconds. For the present purposes, the mean contact time is the period of time from the commencement of mixing of the starting materials to the time when the reaction mixture leaves the reaction space and goes to the work-up stage. In a preferred embodiment, the flow in the process of the invention has a Bodenstein number of more than 10, preferably more than 100 and particularly preferably more than 500.

In a preferred embodiment, the dimensions of the reaction space and the flow velocity are selected so that turbulent flow, i.e. flow having a Reynolds number of at least 2300, preferably at least 2700, of the reaction mixture occurs, with the Reynolds number being formed using the hydraulic diameter of the reaction space.

The gaseous reactants preferably pass through the reaction space at a flow velocity of from 3 to 400 meters/second, preferably from 10 to 250 meters/second. As a result of the turbulent flow, a narrow residence time with a low standard deviation of usually not more than 6% as described in EP 570799 and good mixing are achieved. Measures such as the constriction described in EP-A-593 334, which is also susceptible to blockage, are not necessary.

The reaction volume can be heated/cooled via its outer surface. To build production plants having a high plant capacity, a plurality of reactor tubes can be connected in parallel. However, the reaction can also preferably be carried out adiabatically. This means that no heating or cooling energy streams flow as a result of engineering measures through the outer surface of the reaction volume. The reaction preferably takes place adiabatically.

The process of the invention is preferably carried out in a single stage. For the purposes of the present invention, this means that the mixing and reaction of the starting materials occurs in one step and in one temperature range, preferably in the abovementioned temperature range. Furthermore, the process of the invention is preferably carried out continuously.

After the reaction, the gaseous reaction mixture is preferably quenched with a solvent at temperatures of greater than 130° C. Preferred solvents are hydrocarbons which may optionally be substituted by halogen atoms, for example chlorobenzene, dichlorobenzene and toluene. A particularly preferred solvent is monochlorobenzene. It is also possible to use the isocyanate as solvent. In the scrub/quench, the isocyanate is selectively transferred into the scrubbing solution. The remaining gas and the scrubbing solution obtained are then preferably separated into isocyanate, solvent, phosgene and hydrogen chloride by means of rectification. Preference is given to using the isocyanate.

After the reaction mixture has been reacted in the reaction space, it is passed to the work-up apparatus comprising the quench. This is preferably a scrubbing tower in which the isocyanate formed is separated from the gaseous mixture by condensation in an inert solvent while excess phosgene, hydrogen chloride and, if appropriate, the inert medium pass through the work-up apparatus in gaseous form. Preferred inert solvents are hydrocarbons which may optionally be substituted by halogen atoms, for example chlorobenzene, dichlorobenzene and toluene. The temperature of the inert solvent is preferably kept above the melting point of the carbamyl chloride corresponding to the amine. The temperature of the inert solvent is particularly preferably kept above the dissolution temperature of the carbamyl chloride corresponding to the amine in the quenching medium selected.

Scrubbing can, for example, be carried out in a stirred vessel or in other conventional apparatuses, e.g. in a column or mixer-settler apparatus.

In process engineering terms, all extraction and scrubbing processes and apparatus known per se can be used for a scrub in the process of the invention, e.g. those which are described in Ullmann's Encyclopedia of Industrial Chemistry, 6th ed, 1999 Electronic Release, chapter: Liquid—Liquid Extraction—Apparatus. For example, these can be single-stage or multistage, preferably single-stage, extractions and also those operated in cocurrent or countercurrent, preferably countercurrent.

A suitable quench is known, for example, from EP-A1 1403248, column 2, line 39-column 3, line 18, which is hereby expressly incorporated by reference into the present disclosure.

In this quenching zone, the reaction mixture, which consists essentially of the isocyanates, phosgene and hydrogen chloride, is intensively mixed with the liquid sprayed in. Mixing is carried out so that the temperature of the reaction mixture is reduced from an initial 200-570° C. to 100-200° C., preferably to 140-180° C., and the isocyanate comprised in the reaction mixture is transferred completely or partly by condensation into the liquid droplets sprayed in, while the phosgene and the hydrogen chloride remain essentially completely in the gas phase.

The proportion of the isocyanate comprised in the gaseous reaction mixture which goes over into the liquid phase in the quenching zone is preferably from 20 to 100% by weight, particularly preferably from 50 to 99.5% by weight and in particular from 70 to 99% by weight, based on the isocyanate comprised in the reaction mixture.

The reaction mixture preferably flows through the quenching zone from the top downward. Below the quenching zone, there is a collection vessel in which the liquid phase is precipitated, collected and removed from the reaction space via an outlet and is subsequently worked up. The remaining gas phase is discharged from the reaction space via a second outlet and is likewise worked up.

The quench can, for example, be carried out as described in EP 1403248 A1 or as described in the unpublished German patent application number 10 2004 030164.6 filed on Jun. 22, 2004.

The liquid droplets are for this purpose produced by means of single-fluid or two-fluid atomizer nozzles, preferably single-fluid atomizer nozzles, and, depending on the embodiment, form a spray cone angle of from 10 to 140°, preferably from 10 to 120°, particularly preferably from 10° to 100°.

The liquid which is sprayed in via the atomizer nozzles has to have a good solvent capability for isocyanates. Preference is given to using organic solvents. Particular preference is given to using aromatic solvents which may be substituted by halogen atoms. Examples of such liquids are toluene, benzene, nitrobenzene, anisole, chlorobenzene, dichlorobenzene (ortho, para), trichlorobenzene, xylene, hexane, diethyl isophthalate (DEIP), tetrahydrofuran (THF), dimethylformamide (DMF) and mixtures thereof, preferably monochlorobenzene.

In a particular embodiment of the process of the invention, the liquid sprayed in is a mixture of isocyanates, a mixture of isocyanates and solvent or isocyanate, with each of the quenching liquids used being able to comprise proportions of low boilers such as HCl and phosgene. Preference is given to using the isocyanate which is prepared in the respective process. Since the reaction is stopped by the drop in temperature in the quenching zone, secondary reactions with the isocyanates sprayed in can be ruled out. The advantage of this embodiment is, in particular, that it is not necessary to separate off the solvent.

In an alternative preferred embodiment, the inert medium which is used together with at least one of the starting materials and the solvent used in the quench are the same compound, in which case very particular preference is given to using monochlorobenzene.

Small amounts of by-products which remain in the isocyanate can be separated off from the desired isocyanate by means of additional rectification, by stripping with an inert gas or by crystallization, preferably by rectification.

In the subsequent optional purification step, the isocyanate is separated off from the solvent, preferably by distillation. Here, remaining impurities comprising hydrogen chloride, inert medium and/or phosgene can likewise be separated off, as described, for example, in DE-A1 10260092.

Streams which consist essentially of phosgene and/or hydrogen chloride gas are obtained from the quench and/or the purification stage. According to the invention, hydrogen chloride is separated off from the phosgene from at least part of these streams comprising phosgene and/or hydrogen chloride gas, so that the mass fraction of hydrogen chloride in the phosgene-comprising stream after, if appropriate, mixing with fresh phosgene and before mixing with the amine-comprising stream is less than 15% by weight, preferably less than 10% by weight, particularly preferably less than 5% by weight.

The phosgene-comprising gas stream preferably has a content by mass of hydrogen chloride of at least 0.0001% by weight, particularly preferably at least 0.01% by weight, very particularly preferably at least 0.1% by weight and in particular at least 0.25% by weight.

The separation of the mixture comprising hydrogen chloride and/or phosgene and/or solvent is preferably carried out by distillation and/or by means of a scrub. The separation is preferably carried out by means of a combination of a distillation and a scrub.

Preferred scrubbing media are the solvents mentioned above as quenching media. Particular preference is given to using the same solvents as scrubbing medium and quenching medium.

In a combined scrub and distillation, phosgene is scrubbed from the stream comprising hydrogen chloride by scrubbing with a scrubbing medium, preferably toluene, chlorobenzene or dichlorobenzene, particularly preferably chlorobenzene. This results in a scrubbing medium laden with phosgene and hydrogen chloride. The separation of phosgene and HCl from this laden scrubbing medium after the scrub is preferably carried out by distillation. Here, the separation is, according to the invention, carried out so that a phosgene stream which, if appropriate, after mixing with fresh phosgene has an HCl content of less than 15% by weight is obtained.

The scrub and the distillation are carried out at pressures of from 1 to 10 bar absolute, preferably from 1 to 5 bar absolute.

The hydrogen chloride/phosgene separation can be followed by an adsorption unit, preferably an activated carbon filter, in the hydrogen chloride stream discharged from the separation so as to remove traces of the scrubbing medium from the hydrogen chloride obtained.

A preferred embodiment of the process of the invention is shown schematically in FIG. 1.

In FIG. 1, the reference numerals have the following meanings:
I amine reservoir
II phosgene reservoir
III mixing unit
IV reaction space
V work-up stage (quench)
VI purification stage
VII phosgene-hydrogen chloride separation
1 solvent feed
2 amine feed
3 inert medium feed
4 phosgene feed
4a inert medium feed
5 hydrogen chloride, phosgene and/or inert medium/solvent discharge
6 inert medium/solvent discharge (optional)
7 isocyanate discharge
8 phosgene recirculation
9 hydrogen chloride discharge In the amine reservoir, the amine is brought into the gas phase, if appropriate together with an inert medium such as nitrogen as carrier gas, and fed into the mixing unit III. Phosgene from the phosgene reservoir II is likewise fed into the mixing unit III. After mixing in the mixing unit, which can consist of, for example, a nozzle or a static mixer, the gaseous mixture of phosgene, amine and, if appropriate, inert medium is transferred into the reaction zone IV. As shown in FIG. 1, the mixing unit does not have to be an independent reaction stage, but instead it can be advantageous to integrate the mixing unit into the reaction zone.

After the reaction mixture has been reacted in the reaction zone, it goes to the work-up stage. This is preferably a scrubbing tower in which the isocyanate formed is separated off from the gaseous mixture by condensation in an inert solvent, while excess phosgene, hydrogen chloride and if appropriate the inert medium pass in gaseous form through the work-up stage. As inert solvent, preference is given to aromatic hydrocarbons which may optionally be substituted by halogen atoms, for example chlorobenzene or dichlorobenzene and toluene. The temperature of the inert solvent is particularly preferably kept above the dissolution temperature of the carbamoyl chloride corresponding to the amine in the quenching medium selected.

In the subsequent purification stage, the isocyanate is separated off from the solvent, preferably by distillation. Residual impurities, for example hydrogen chloride, inert medium and/or phosgene, can likewise be separated off here.

According to the invention, at least one phosgene-comprising substream 5 which comes from the purification stage and/or the work-up stage and comprises phosgene is at least partially freed of hydrogen chloride comprised therein and is recirculated to the reaction. For this purpose, it is combined with the fresh phosgene stream 4 or with the phosgene stream to the mixing device III.

Phosgene recycle stream 8 and fresh phosgene stream 4 are preferably mixed in such a ratio that the stoichiometry desired in the reaction is achieved.

In a further, preferred embodiment, HCl is removed from the substream 5 in at least such an amount that the above-described criterion is met.

The HCl can be removed by distillation and/or by means of a scrub. If the separation is effected by means of a scrub and a solvent is at the same time used for scrubbing out the isocyanate at the end of the reaction section in the process, then the solvent for scrubbing out the isocyanate is preferably used as scrubbing medium for separation of the HCl/phosgene mixture.

EXAMPLES

Example 1

According to the Invention

A 1,6-diaminoohexane (HDA)-comprising stream having a mass flow of 5.4 kg/hr, which has been premixed with monochlorobenzene (MCB), and a phosgene-comprising stream having a mass flow of 16.7 kg/hr, which has been premixed with hydrogen chloride (HCl), are fed into a laboratory tube reactor having a diameter of 12 mm and a length of 1 m. An inlet temperature of 410° C. is set for both feed streams. The tube reactor is heated by means of supplementary heating so that operation is adiabatic.

The HDA-comprising stream has an HDA content of 32.5% by mass of HDA and a monochlorobenzene content of 67.5% by mass of MCB.

The phosgene-comprising stream is set so that an HCl content of 10% by mass is obtained in the HCl/phosgene mixture. The HDA-comprising stream is introduced into the reaction tube via an inlet tube. A pressure of 1.3 bar absolute is set at the outlet of the tube reactor by means of a pressure regulator.

The experiment can be carried out for 3 days without an appreciable increase in pressure in the feed lines.

Example 2

Comparative Example, Not According to the Invention

An HDA-comprising stream having a mass flow of 5.4 kg/hr, which has been premixed with monochlorobenzene, and a phosgene-comprising stream having a mass flow of 18.75 kg/hr, which has been premixed with hydrogen chloride, are fed into a laboratory tube reactor having a diameter of 12 mm and a length of 1 m. An inlet temperature of 410° C.

is set for both feed streams. The tube reactor is heated by means of supplementary heating so that operation is adiabatic.

The HDA-comprising stream has an HDA content of 32.5% by mass of HDA and a monochlorobenzene content of 67.5% by mass of MCB.

The phosgene-comprising stream is set so that an HCl content of 20% by mass is obtained in the HCl/phosgene mixture.

The HDA-comprising stream is introduced into the reaction tube via an inlet tube. A pressure of 1.3 bar absolute is set at the outlet of the tube reactor by means of a pressure regulator.

Solids formation occurs in the tube in the region of the point of introduction of the HDA; this was measured via an increase in the pressure built up in the feed lines to the reactor. The experiment is stopped after one hour./

The invention claimed is:

1. A process for preparing a diisocyanate, the process comprising
reacting a diamine with a stoichiometric excess of phosgene in a reaction zone, to form the diisocyanate,
wherein
the diamine, diisocyanate and phosgene are in a gaseous state in the reaction zone,
in the reaction zone, a gaseous reaction mixture comprising unreacted excess phosgene, hydrogen chloride gas (HCl), and the diisocyanate is formed from the reaction of the diamine with some of the phosgene,
the gaseous reaction mixture is transferred out of the reaction zone,
the unreacted excess phosgene, and the hydrogen chloride gas (HCl) are separated from diisocyanate to form a precursor recirculation stream comprising the separated excess phosgene and hydrogen chloride gas, but not the diisocyanate,
some of the hydrogen chloride gas is separated off from the precursor recirculation stream to form a recirculation stream comprising the separated excess phosgene and the remaining hydrogen chloride gas, but not the diisocyanate,
wherein the mass fraction of the remaining hydrogen chloride gas in the recirculation stream is less than 15% by weight and at least 0.001% by weight, and
the recirculation stream is at least partly recirculated to the reaction zone.

2. The process according to claim 1, wherein the mass fraction of the remaining hydrogen chloride gas in the recirculation stream is less than 15% by weight and at least 0.01% by weight.

3. The process according to claim 1, wherein before entering into the reaction zone, at least one inert medium is added to the diamine and/or the stoichiometric excess of phosgene so that the gas volume of inert medium to the diamine and/or to the stoichiometric excess of phosgene is greater than 0.0001 and up to 30.

4. The process according to claim 1, wherein some of the phosgene reacts with diamine in the reaction zone at absolute pressures of from >0.1 bar to <20 bar.

5. The process according to claim 1, wherein some of the phosgene reacts with diamine in the reaction zone at temperatures of from >200° C. to 600° C.

6. The process according to claim 1, wherein the mean contact time of the gaseous reaction mixture in the reaction zone ranges from 0.001 seconds to <5 seconds.

7. The process according to claim 1, wherein the molar ratio of the stoichiometric excess phosgene to amino groups on the diamine is from 1.1:1 to 20:1.

8. The process according to claim 1, wherein a flow in the reaction zone has a Bodenstein number of more than 10.

9. The process according to claim 3, wherein the inert medium is chlorobenzene.

10. The process according to claim 1, wherein the phosgene, the diamine and the diisocyanate remain in the gas phase to an extent of at least 95% while passing through the reaction zone.

11. The process according to claim 1, wherein the diisocyanate is selected from the group consisting of 1,6-diisocyanatohexane, 1-isocyanato-3,3,5-trimethyl-5-(isocyanatomethyl)cyclohexane, 4,4'-di(isocyanatocyclo-hexyl)-methane and tolylene diisocyanate isomer mixtures.

12. The process of claim 6, wherein the mean contact time ranges from 0.01 to 3 seconds.

13. The process of claim 6, wherein the mean contact time ranges from 0.02 to 1.5 seconds.

14. The process of claim 1, wherein some of the phosgene reacts with diamine in the reaction zone at absolute pressures of from 0.5 bar to 10 bar.

15. The process of claim 1, wherein some of the phosgene reacts with diamine in the reaction zone at absolute pressures of from 0.7 bar to 5 bar.

16. The process of claim 1, wherein some of the phosgene reacts with diamine in the reaction zone at absolute pressures of from 0.8 bar to 3 bar.

17. The process of claim 1, wherein the diamine is 1,6-diaminohexane.

18. The process of claim 1, wherein the diamine is an aliphatic diamine.

19. The process of claim 1, wherein the diamine is 2,6-toluenediamine.

20. The process of claim 1, wherein the diamine is an aromatic diamine.

21. The process of claim 1, wherein the mass fraction of the remaining hydrogen chloride gas in the recirculation stream ranges from less than 15% by weight to 10% by weight.

* * * * *